United States Patent
O'Brien et al.

(10) Patent No.: US 9,151,709 B2
(45) Date of Patent: Oct. 6, 2015

(54) MULTIPLE PHASE FLOW SYSTEM FOR DETECTING AND ISOLATING SUBSTANCES

(75) Inventors: Christine Mary O'Brien, St. Louis, MO (US); Sagar K. Gupta, Columbia, MO (US); John Andrew Viator, Columbia, MO (US); Shramik Sengupta, Columbia, MO (US); Jeff Mosley, New Bloomfield, MO (US); Kyle Rood, Saint Peters, MO (US)

(73) Assignee: The Curators of the University of Missouri, Columbia, MO (US)

( * ) Notice: Subject to any disclaimer, the term of this patent is extended or adjusted under 35 U.S.C. 154(b) by 434 days.

(21) Appl. No.: 13/228,428

(22) Filed: Sep. 8, 2011

(65) Prior Publication Data
US 2012/0064566 A1    Mar. 15, 2012

Related U.S. Application Data

(60) Provisional application No. 61/381,809, filed on Sep. 10, 2010.

(51) Int. Cl.
| | | |
|---|---|---|
| *G01N 21/03* | (2006.01) | |
| *G01N 21/17* | (2006.01) | |
| *G01N 21/05* | (2006.01) | |
| *B01F 13/00* | (2006.01) | |

(52) U.S. Cl.
CPC ......... *G01N 21/1702* (2013.01); *B01F 13/0071* (2013.01); *G01N 21/05* (2013.01); *G01N 2021/1708* (2013.01)

(58) Field of Classification Search
CPC ............... G01N 2021/1702; G01N 2021/1708
See application file for complete search history.

(56) References Cited

U.S. PATENT DOCUMENTS

| | | | |
|---|---|---|---|
| 3,668,936 A * | 6/1972 | Herron | 73/864.22 |
| 3,698,870 A | 10/1972 | De Jong | |
| 4,436,428 A * | 3/1984 | Watanabe et al. | 356/432 |
| 6,108,096 A * | 8/2000 | Ushio et al. | 356/432 |
| 6,284,546 B1 * | 9/2001 | Bryning et al. | 436/172 |
| 2004/0039379 A1 | 2/2004 | Viator et al. | |
| 2007/0179435 A1 | 8/2007 | Braig et al. | |

(Continued)

FOREIGN PATENT DOCUMENTS

| | | |
|---|---|---|
| WO | 9631782 A1 | 10/1996 |
| WO | 200808402 A2 | 10/1996 |
| WO | 200559512 A2 | 6/2005 |

OTHER PUBLICATIONS

International Preliminary Report on Patentability mailed Mar. 12, 2013 in Application No. PCT/US2011/051220; 7 pages.

(Continued)

*Primary Examiner* — Paul Hyun
(74) *Attorney, Agent, or Firm* — Shook, Hardy & Bacon L.L.P.

(57) ABSTRACT

A multiple flow system and method for detecting substances in a fluid is provided. More specifically, a first fluid tube containing a first fluid and a second fluid tube containing a second fluid are coupled to a common fluid tube via a connector, such that alternating discrete compartments of the first fluid and the second fluid flow through the common fluid tube. The first and second fluids are immiscible. A substance detector, having a flow chamber with an internal wall, is coupled to the common fluid tube. The alternating discrete compartments of the first and second fluids flow through the flow chamber and are analyzed by the substance detector.

17 Claims, 10 Drawing Sheets

(56) References Cited

U.S. PATENT DOCUMENTS

2009/0024038 A1*  1/2009  Arnold .................. 600/459
2009/0170149 A1   7/2009  Viator et al.
2010/0209916 A1   8/2010  Zon

OTHER PUBLICATIONS

PCT International Search Report and Written Opinion of the International Searchign Authority, or the Declaration, mailed Jan. 18, 2012 regarding PCT Appln. PCT/US/1151220 11 pages.
Petersen K. et al: "An air-carrier continuous analysis system", Talanta, Elsevier, Amsterdam, NL, vol. 36, No. 1-2, Jan. 1, 1989, pp. 49-61, XP026575794, ISSN: 0039—140 (89) 80081-5 [retrieved on Jan. 1, 1989] *abstract; figures 1, 3, 6.
Miro et al.: Miniaturization of environmental chemical assays in flowing systems: The lab-on-a-valve approach vis-à-vis lab-on-a-chip microfluidic deices:, Analytica Chimica Acta, Elsevier, Amsterdam, NL. vol. 600, No. 1-2, Sep. 26, 2007, pp. 46-57,, XPO2286323, issn: 003-2670, D01: 10.1016/J.ACA.2007.02.035 * figures 2, 3*.
Supplementary European Search Report mailed Mar. 7, 2014 in European Patent Application No. 11/824237.9.
China Patent Appl. No. 201180048895.0 Notice of First Office Action dated Feb. 18, 2014.
Liangzhong; "Use of photoacoustic imaging in cancer early detection and treatment monitoring"; Chinese Master's Theses Full-text Database; E072-17; Published Dec. 15, 2007, 58 pages.
Weight et al., "Photoacoustic detection of metastatic melanoma cells in the human circulatory system"; Optics Letters, vol. 31, No. 20, Oct. 15, 2006, pp. 2998-3000.
Third Office Action issued Feb. 13, 2015 in Chinese Patent Application No. 201180048895.0, 24 pages.

* cited by examiner

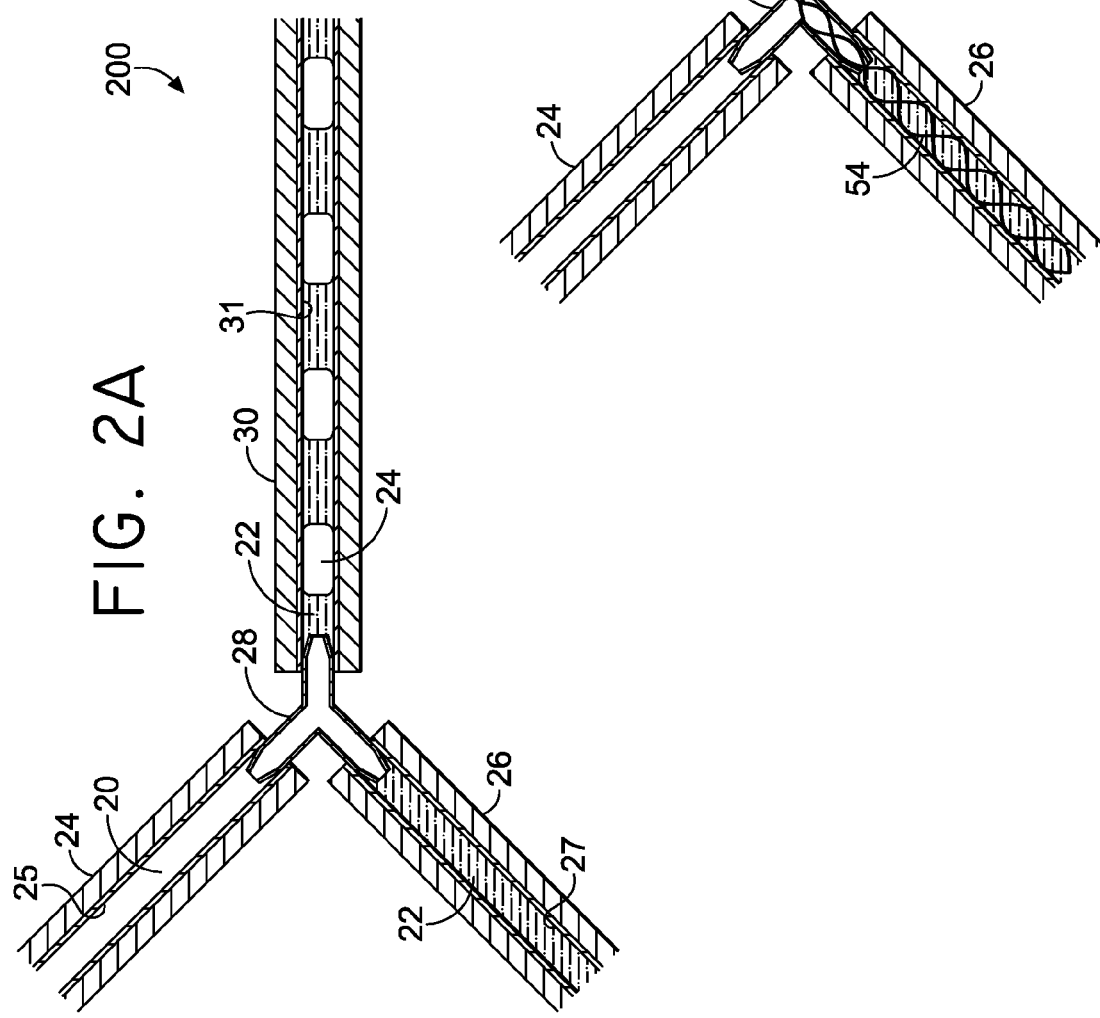

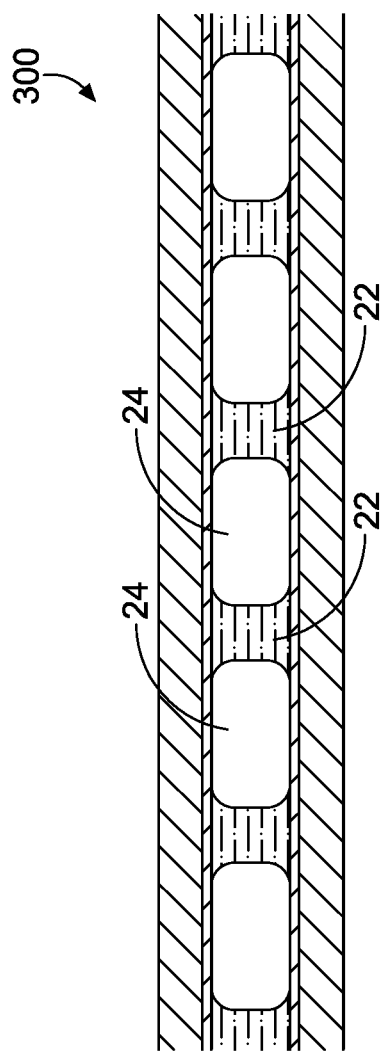
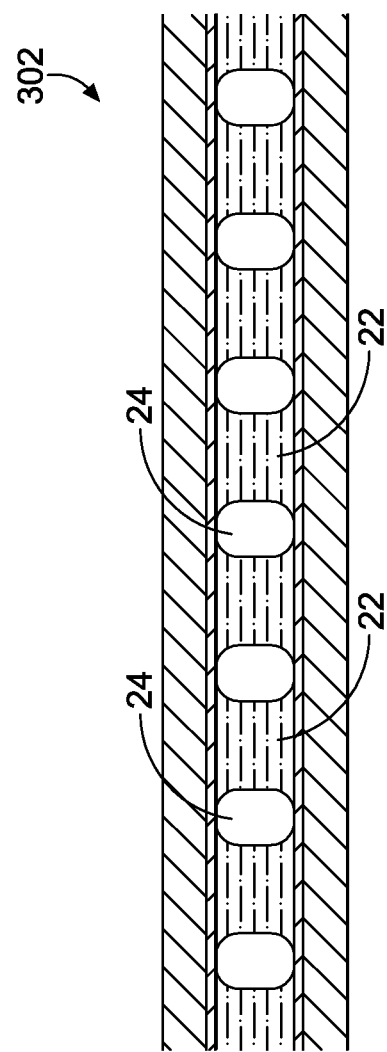

MULTIPLE PHASE FLOW SYSTEM FOR DETECTING AND ISOLATING SUBSTANCES

CROSS-REFERENCE TO RELATED APPLICATIONS

This application claims priority to U.S. Provisional Application Ser. No. 61/381,809 entitled "MULTIPLE PHASE FLOW SYSTEM FOR DETECTING AND ISOLATING SUBSTANCES," filed Sep. 10, 2010, the disclosure of which is hereby incorporated by reference as if set forth in its entirety herein.

STATEMENT REGARDING FEDERALLY SPONSORED RESEARCH OR DEVELOPMENT

This invention was made with grant support under Grant No. R21CA139186-0, awarded by the National Institute of Health (NIH). The government has certain rights in this invention.

BACKGROUND

Melanoma is the most deadly form of skin cancer. Although melanoma has a relatively low death rate compared with other cancers as it is generally easy to see on the skin and can be simply removed, it quickly becomes deadly if the superficial tumor metastasizes to other parts of the body. In metastasis, circulating melanoma cells (CMCs), cells that have broken off from the original tumor site and move through the blood or lymphatic system, can plant themselves elsewhere and create secondary tumors that are subsequently the cause for terminal melanoma. Accordingly, early diagnosis will likely be the cure to cancer, as the treatments have higher chances of success because the cancer has not fully manifested itself yet.

Furthermore, it is predicted that in 2010 over 68,000 Americans will be diagnosed with the disease and over 8,000 melanoma patients will die from the illness. Nevertheless, melanoma can be easily cured if it is detected early and quickly removed from the skin; however, if it metastasizes, the cancer can become lethal. Considering that a 1 mm diameter tumor typically consists of one million cells, larger more visible tumors can generally consist of billions of cells. That said, a patient who is diagnosed from a large tumor will have reduced options and will necessitate more physically demanding treatment than a patient who is diagnosed before secondary tumors can form. Unfortunately, patients must currently wait months to know if the superficial melanoma tumor has spread, because the current methods of diagnosing metastatic cancer are through imaging techniques, which require the presence of a visible metastatic tumor. Consequently, patients are oftentimes diagnosed too late.

Current methods for diagnosing metastatic cancer include lymph node biopsies and imaging techniques. However, lymph node biopsies can produce false negatives if the cancer did not interact with the lymphatic system and cannot be performed numerous times for disease monitoring. That said, circulating tumor cells can be an excellent source of information for diagnosis and monitoring of metastatic melanoma and other pathological diseases if they can be detected in the lymphatic system or blood stream. For that reason, many techniques are being investigated to detect and isolate these cells for both diagnostic and disease monitoring purposes. Some research has already been conducted to find CMCs, including RT-PCR, immunohistochemistry, magnetic cell sorting, fiber optic array scanning technology, and microfilters; however, high false negative rates, labeling, and long procedures limit chances of clinical implementation.

Unfortunately, the current methods used to diagnose metastatic disease are not sensitive to single metastatic cells. Patients must wait until secondary tumors are formed before they can be diagnosed and begin life saving treatment.

BRIEF DESCRIPTION OF THE SEVERAL VIEWS OF THE DRAWINGS

The present invention is described in detail below with reference to the attached drawing figures, wherein:

FIG. 2A is an expanded view of a connection of a multiple phase flow system with the top portion of the body removed to expose the channel and fluids in accordance with an embodiment of the invention;

FIG. 2B is an expanded view of a connection of a multiple phase flow system including with the top portion of the body removed to expose the channel, fluids and optical waveguide in accordance with an embodiment of the invention;

FIGS. 3A and 3B are expanded views of a tube containing two fluids, where in the amount of each alternating fluid varies in accordance with embodiments of the invention;

DETAILED DESCRIPTION

Embodiments of the present invention are directed to a label-free method to detect melanoma in vitro in combination with an isolation method that is simple, has a low margin for error, and effective. Metastatic melanoma cells are detected and then isolated from a patient sample, such as a centrifuged blood sample. Isolation of melanoma cells will aid not only in early diagnosis of the patient but there is a positive correlation between the number of circulating tumor cells present in the blood and the prognosis of the patient. Detection of circulating melanoma cells, cells that have broken off from the original tumor site and move through the blood or lymph system, can be diagnostic and monitoring tools for cancer. Being able to isolate and count melanoma cells could be used for monitoring therapies of cancer patients; high cell counts would indicate a severe prognosis, whereas low cell counts would indicate that the treatment is working well.

Detection of metastatic melanoma in the blood is imperative because it eliminates the waiting game for cancer patients. Using embodiments of the present invention, patients can have a simple blood sample scanned for cancer as often as desired instead of waiting months to see if a tumor is visible on a scan. These months could have been spent providing the patients with life saving therapies, as opposed to waiting to see if the cancer has spread, or monitoring whether current therapies are working.

Embodiments of the present invention decrease potential error involved with a normal flow system and allow for preliminary isolation of metastatic melanoma from the patient sample. In one embodiment, the detector includes a laser, transducer, and oscilloscope.

Figure 1:
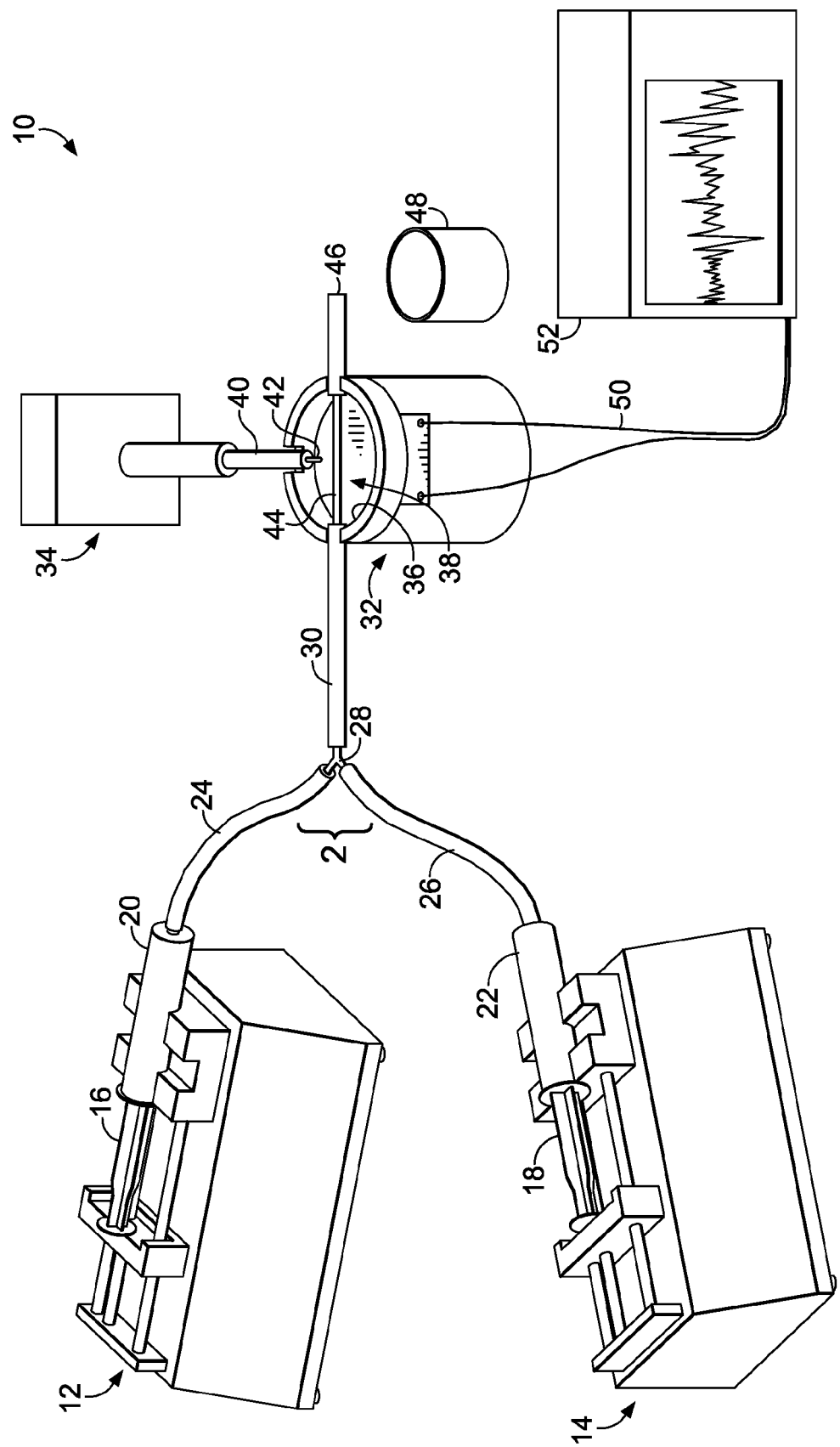
FIG. 1 is a perspective view of a multiple phase flow system for isolating substances in accordance with an embodiment of the invention.

Having briefly described an overview of embodiments of the present invention, exemplary figures depicting embodiments of the present invention are described in order to provide a general context for various aspects of the present invention. With reference to FIGS. 1-4 in particular, where like reference numerals identify like elements in the various views, an exemplary multiple phase flow system 10 is illustrated. Multiple phase flow system 10 generally includes a first pump 12, a second pump 14, a first fluid tube 24, a second fluid tube 26, a connector 28, a multiple fluid tube 30 and a substance detector 32. Although depicted as having two pumps, it will be appreciated that multiple phase flow system 10 may include any number of pumps. First pump 12 and second pump 14 are depicted in FIG. 1 as being syringe pumps. However, it will be appreciated that any type of device that is used for the movement of fluids may be utilized as a pump. The flow rate for the multiple phase flow system used ranges from 0-1000 μL/sec. In further embodiments, the movement of fluids through the multiple phase flow system is based on pressure driving the flow of the respective fluid through the system. For example, the one or more fluids may be flowing through the multiple phase flow system based on gravity, resulting in an elevation head for the fluid.

With reference to FIG. 2, tubes 24, 26 and 30 are a long hollow and typically cylindrical object, used for the passage of fluids. In one embodiment, tubes 24, 26 and 30 are silicone tubing.

Figure 4:
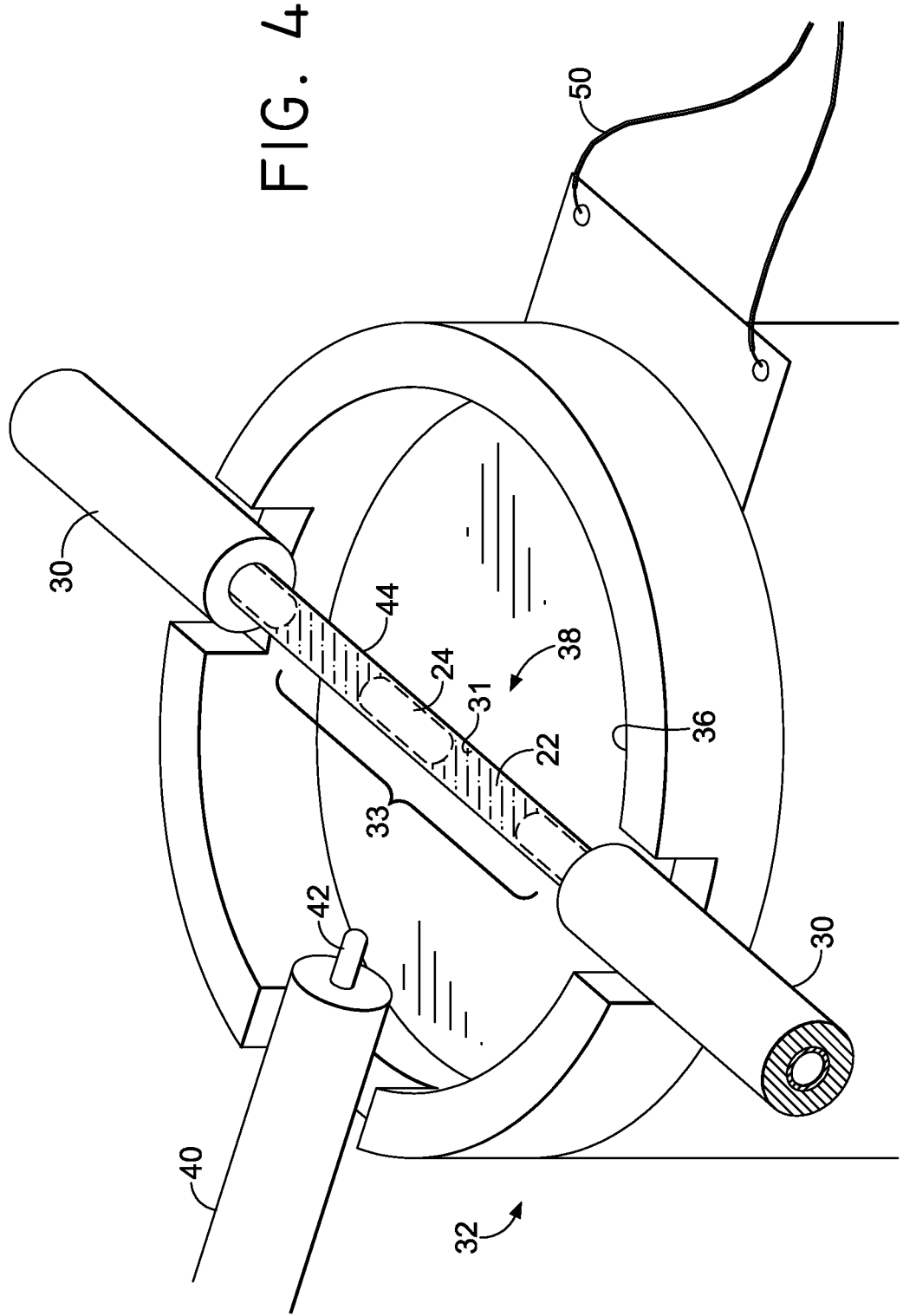
FIG. 4 is an expanded perspective view of a detection chamber of a multiple phase flow system in accordance with an embodiment of the invention.

Referring briefly to FIG. 4, the flow chamber 33 within the detector chamber 38 is made from acrylamide gel shaped around a wire or other tube. The acrylamide gel is allowed to harden or solidify and the wire is removed to create a channel, such as flow chamber 33 defined by an internal wall, for fluid to flow through when it is within the detection chamber 38. It will be appreciated that any variety of other methods and materials may be used to create flow chamber 33, for fluid to flow through. In embodiments, flow chamber 33 is made from a material having an acoustic impedance close to the acoustic impedance of water. The multiple phase flow system 10 has an inner flow diameter of the flow chamber 33 from about 0-10 mm in diameter. The acrylamide is used as an acoustic path from the excited cell to the acoustic sensor.

With reference to FIGS. 1 and 2, a first fluid 20 and a second fluid 22 are fed from their respective tubes 24 and 26 into common fluid tube 30 using a connector 28. A fluid is any state of matter which can flow with relative ease and tends to assume the shape of its container and may include a liquid, gas or plasma. In this embodiment, first fluid 20 is different from the second fluid 22 and is immiscible and/or creates bubbles with second fluid 22. For example, first fluid 20 may be air while second fluid 22 is water or other fluid creating gas bubbles of the first fluid 20 within the second fluid 22. In another example, first fluid 20 is oil while second fluid 22 is water or hydrophilic liquid. While FIGS. 1 and 2 are depicted as having a first and second fluid, it will be appreciated that any number of multiple different fluids may be utilized in embodiments of the present invention. For example, a third fluid may flow into common fluid tube 30 via connector 28.

Figure 8:
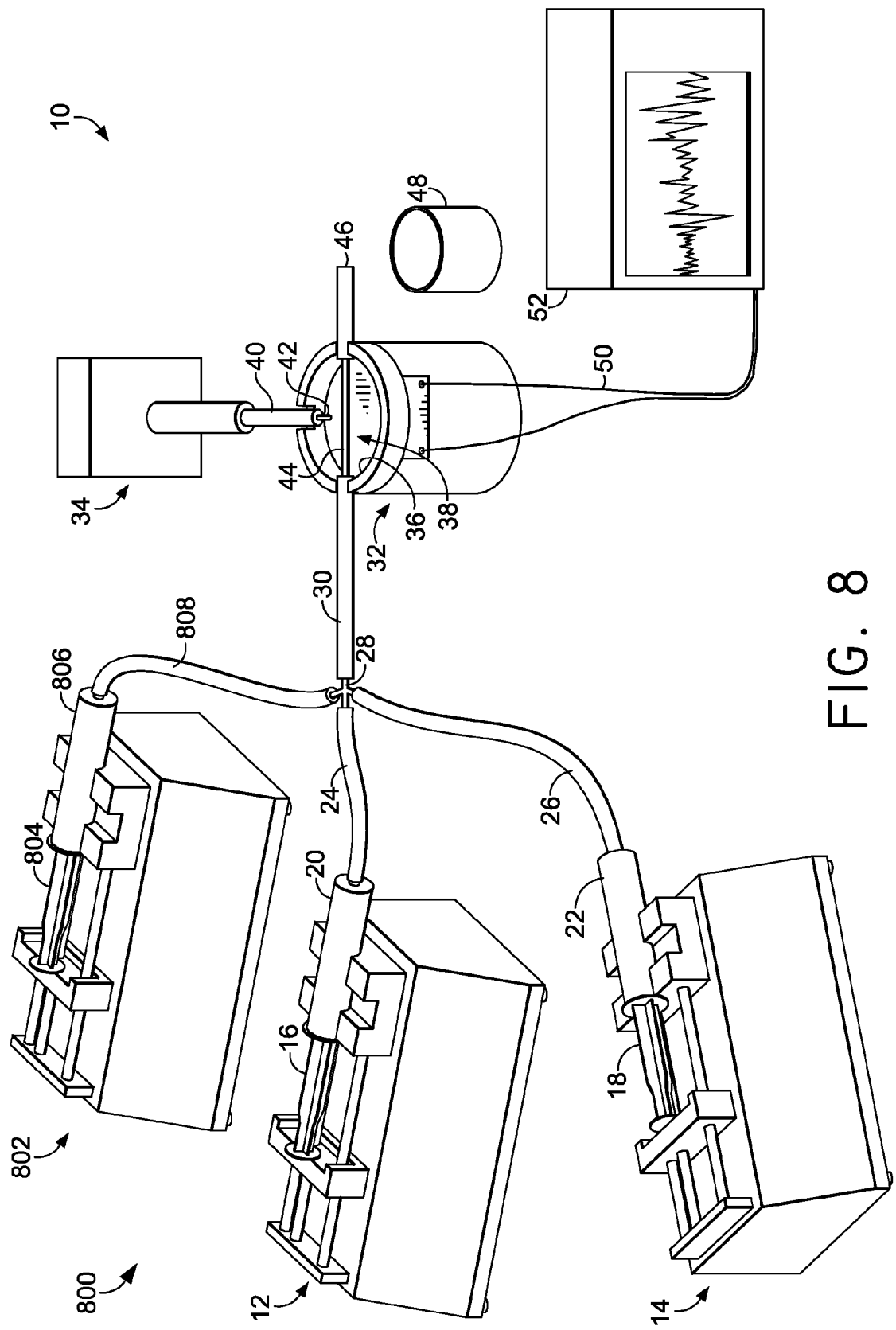
FIG. 8 is a perspective view of a multiple phase flow system for isolating substances in accordance with an embodiment of the invention.

As such, as shown in the multiple phase flow system 800 of FIG. 8, a third pump 802 may include a tube 808 coupled to the connector 28.

First fluid 20 and second fluid 22 are fed into a common fluid tube 30 using a connector 28. Common fluid tube 30 is a common channel for the fluids to flow through. The connector 28 depicted in FIGS. 1 and 2 is a Y connector. It will be appreciated that the connector may be any shape, including a Y connector or T connector that allows for the first fluid 20 and second fluid 22 to be forced together into a single flow path without mixing together. In one embodiment, the multiple phase flow system may use three fluids, two of which mix together in the common fluid tube 30 while remaining separate from the third fluid. For example, if the three fluids are water, alginate and air, the water and alginate may be mixed together to form a gel discrete compartment and that remains separate from the air discrete compartment. In further embodiments, instead of two tubes meeting at a common tube, a multiple phase flow may be created based on multiple tubes meeting at the common fluid tube 30.

First fluid 20 and second fluid 22 essentially take turns entering the common fluid tube 30 due to the immiscibility (e.g., oil and water) and/or gas bubble creation (e.g., air and water) of the two fluids. In one embodiment, the immiscibility is due to the hydrophobicity of the first fluid (such as oil) and the hydrophilicity of the second fluid (such as water soluble fluid). As the first fluid 20 enters common fluid tube 30, second fluid 22 builds up pressure until the first fluid 20 stops flowing and second fluid 22 has its turn to flow. This creates alternating discrete compartments of first fluid 20 and second fluid 22 respectively. By introducing two fluids through a connector, such as a T-junction into a single flow path, a substance is compartmentalized. This is ideal because the exact discrete compartment of a first fluid or second fluid in which the substance to be detected is located can be identified and easily extracted. It will be appreciated that the discrete compartments of the first fluid 20 and second fluid 22 as shown in FIGS. 3A and 3B may vary in size depending on the diameter of common fluid tube 30 and flow rate of the fluids may be from 0-1 ml/s in size. Furthermore, more than two fluids may be utilized and biological fluids from multiple patients may also be used and separated in alternating discrete compartments.

In embodiments, first fluid 20 is a separator fluid such as air, gas and/or oil for creating discrete compartments of second fluid 22. Second fluid 22 may include any type of fluid that includes a substance to be detected. In one embodiment, second fluid 22 may be any type of fluid containing a biological material or substance, such as cancer cells (breast cancer, melanoma, prostate cancer and the like), tissue, cells, pathogens, microorganisms (such as malaria), infectious diseases, pigment, non-optically absorbing substances with color inducement (e.g., dyes added to non-colored cancer cells or gold nanoparticles added to cells), compounds, non-biological substances and/or foreign bodies from an individual's biological sample including, but not limited to, blood, saliva, urine, fecal material, serum, plasma, tissue and spinal fluid. In another embodiment, second fluid 22 is a non-biological fluid containing biological or non-biological substances such as detecting lead (substance) in water (second fluid). As will be described in more detail below, in one embodiment second fluid 22 is centrifuged white blood cell solution of an individual which may or may not contain melanoma cells. In one embodiment, whole blood samples are taken from melanoma patients and centrifuged, leaving any melanoma in a white blood cell suspension.

The alternating discrete compartments of first fluid 20 and second fluid 22 flow through common tube 30 into the flow chamber 33 within the detection chamber 38 of detector 32. With reference to FIGS. 1 and 4, generator 34 is a photoacoustic laser source. Detection chamber 38 includes an internal wall 36 defining an open interior of the detection chamber 38. Laser source 34 includes a laser 40 and pulsator 42. Although laser source 34 is depicted in one embodiment to be a photoacoustic detector, it will be appreciated that generator 34 may include any variety of excitation devices and/or mechanisms for converting energy into something that can be further processed to obtain information including radiation, laser, chemical, electrical semiconductor, fluorescence, radio waves, magnetic, tomography, thermography and ultrasound detection.

In one embodiment, a photoacoustic detector can detect or determine whether or not a fluid contains substances having pigment such as metastatic melanoma which inherently contains melanin, a small pigmented granule. As an individual discrete component of fluid passes through flow chamber 33, it is irradiated by photoacoustic laser source 34 with a rapid pulse of light. It will be appreciated that the laser light may be directed transversely to the flow or along the axis of the flow using an optical waveguide as described with respect to FIG. 2B. When melanoma is irradiated with a rapid pulse of intense laser light the melanin undergoes thermo-elastic expansion. Thus, if the discrete component passing through the chamber 33 contains melanoma, the melanin in the melanoma undergoes thermo-elastic expansion and ultimately creates a photoacoustic wave. Irradiated melanoma cells produce photoacoustic waves which are detected with a piezoelectric transducer, while the white blood cells create no signals because they are optically transparent. It will be appreciated that a detector may be used to determine whether or not a fluid passing through the detector in a multiple phase flow system contains a particular substance.

In this embodiment, as shown in and discussed in more detail below with respect to FIGS. 5A-5F, the irradiation volume for each discrete compartment that has been irradiated by intense laser light may be communicated from an acoustic sensor (or other type of sensor) within flow chamber 33 via connection 50 to computer display device 52 or other output device. The irradiation volume for the discrete compartment is displayed on display device 52 and shown and described in more detail below with respect to FIGS. 5A-5F. The irradiation volume graphical displays include a spectrometer before irradiation point to ensure the expected medium is producing signals. Use of the irradiation volumes can allow for single melanoma cell isolation, because when a melanoma cell is detected it can visually be seen which discrete compartment of fluid melanoma cell(s) reside in.

Specific discrete compartment(s) detected to contain the substance being tested for, such as melanoma cell(s), can be extracted. With reference to FIG. 1, a collection container 48 may be used to collect the discrete compartment from the tube exit 46. It will be appreciated that while the collection of the discrete compartment of fluid identified as containing the substance being tested for is depicted as being done manually in collection container 48 in FIG. 1, any variety of collection mechanisms, automatic or manual, may be used to collect the discrete compartment. Furthermore, alternative separate containers (not shown) may be used to collect other discrete compartments that have not tested positive for the substance being tested for. Fluid volumes containing substances, such as melanoma cells, may be sequestered by bubbles, allow for isolation of small volumes of fluid. Whereas, utilizing a continuous flow without bubbles it is difficult to determine what volume of liquid to collect. Collected discrete compartments of fluids can be sent for a variety of testing or further diluted.

The extracted discrete compartment may then be diluted and re-passed through the system 10 and repeated until each separate extraction volume of the second fluid 22 contains a single melanoma cell and no white blood cells. As such, the analysis of samples may be conducted iteratively until a desired concentration of a desired substance is detected and/or isolated. In one embodiment, each iteration of the repeated separation reduces the concentration of undesired particles (such as white blood cells) by a particular factor of dilution. For example, a discrete compartment demonstrating a photoacoustic effect (thus indicating that the discrete compartment contains a melanoma cell) can be diluted and re-passed through the system 10 iteratively until the desired melanoma cell is isolated from other undesired particles. The isolated melanoma cell (or other desired particle) can then be analyzed for particular testing, such as gene expression testing, PCR, and the like.

In embodiments, pigmentation is detected due to photoacoustic thermo-elastic expansion when an absorber is struck with a rapid pulse of light; colorless particles remain acoustically transparent allowing numerous cells to cross the detection beam at a time. Accordingly, a multi-phase flowmetry technique adjunct with photoacoustic detection to detect and capture CMCs in vitro is provided. Capture of the detected melanoma cells not only verifies that melanoma is truly being detected; it will also provide cancer biologists with early stage CMCs to study.

With reference to FIG. 2B, an optical waveguide 54 is produced by the fluid having a higher optical index of refraction than the surrounding material. Fluid that contains the cells could have an index of refraction of 1.39 by adding sugar or polyethylene glycol and the surrounding acrylamide flow chamber may have an index refraction of 1.35. This mismatch allows total internal reflection, making an optical waveguide much like an optical fiber. This allows the alternating components to be an optical wave guide so laser light is filling entire tube and every discrete compartment is filled with laser light. The laser light can irradiate the entire sample due to total internal reflection. Total internal reflection occurs when the light hits a material that has a lower index of refraction than the material it is current moving through. This allows for the laser light to stay inside the medium of choice as long as the index of refraction parameters are met. Therefore, the flow channel is an optical waveguide to ensure the entire discrete compartments are irradiated without wasting any laser energy. This is done in one embodiment by adding sugar, polyethylene or other substance to increase the index of refraction to the second fluid to increase to higher than the index of refraction of acrylamide.

The multi-phase flow system 10 allows for a sample of interest to be run across a detector to identify if a certain analytes and/or substances are present in the sample. Millions of cells can flow past the detector at a time due to the photoacoustic transparency of white blood cells. This allows for large volumes to be scanned very quickly for circulating melanoma cells.

EXAMPLE 1

Multiple Phase Flow Design

The multiple phase flow system utilized in Example 1 comprises cylindrical silicone tubing. However, it will be appreciated that other shapes such as square or rectangular could be used. The multiple phase flow system has an inner flow diameter of the channel of about 1.6 mm in diameter. The multiple phase flow system used ranged from 200-300 μL/min. However, the slugs that formed were only 2-3 microliters and the Capillary and Reynolds number stayed within microfluidic conditions. In addition, high flow rates were used so a large blood volume could be examined quickly.

The system utilized a polyvinylidene fluoride (PVDF) "clip" transducer. The sensor may be any piezoelectric material or other non-piezoelectric sound sensor. It will be appreciated that any material may be used so long as it conducts electrical current. Two brass sheets were cut with a hole in the middle and soldered to a BNC coaxial cable connector. Tape separated the brass sheets and PVDF was placed between the brass covering the holes. The transducer was placed into a Polydimethylsiloxane (PDMS) housing that kept both the transducer and flow chamber stationary. The transducer was fitted into the slit and a PDMS ring was placed above the transducer, exposing the PVDF but covering the brass. The PDMS was used to prevent acoustic reflections from the brass that could interfere with melanoma detection.

Next the flow chamber was placed on top of the PDMS ring such that the chamber was directly aligned with the PVDF element. A frequency-tripled, Q-switched Nd:YAG laser (Continuum) fired at the side of the flow chamber at a right angle from the transducer. The laser pulsed at 532 nm, 20 Hz, and between 5-8 mJ for 5 ns pulse duration.

The flow chamber was connected to two syringe pumps; one syringe contained the cell samples and the other contained air. The air is pumped at 0.2 mL/min and the cell samples are pumped at 0.1 mL/min. The syringe pump that housed the cells was set vertically to ensure the cells did not settle to the bottom, therefore the air needed a higher flow rate to compensate for the increased pressure.

EXAMPLE 2

Sample Preparation

Two-phase flow was created using a T-junction, which combines the two separate phases into one flow path while keeping the phases distinct. The phases chosen for use in Example 2 were both water and oil, and air and water. Air and water produced a water slug could easily be extracted without contaminating the sample with the neighboring phase. However, when using air and water the liquids build up pressure and purge the system. Tween 20 was used in the air/water two-phase flow system to reduce the interfacial tension between the phases. A 2% Tween 20 in PBS buffer was used as the water phase. It will be appreciated that other surfactants, such as 2% Tween 80 may also be used to reduce the tension between the phases.

EXAMPLE 3

Sample Preparation

Biological samples were used to show that the multi-phase system is applicable to a clinical environment. Melanoma cells were cultured at the University of Missouri, and all white blood cell samples were obtained from whole blood donated from lab members. The cell culture and enrichment techniques are described below.

Melanoma Cells Suspended in PBS.

An HS 936 melanoma cell line was cultured for use in photoacoustic experiments. The cells were fixed in ethanol and re-suspended in PBS. Approximately 15 minutes before experiments, the cells were diluted with a phosphate buffered saline (PBS)+2% Tween 20 (Fisher Scientific) solution to the desired cell concentration. The cells were then counted manually using a hemoctyometer.

White Blood Cells Suspended in PBS and Melanoma.

White blood cells suspended in PBS were prepared by first obtaining cancer-free whole blood donated from lab members. The blood was poured into a centrifuge tube that contained Histopaque 1077, a material whose density value is between that of white blood cells and red blood cells, and then centrifuged. The white blood cell layer and the contents adjacent to it were removed and then added to smaller diameter centrifuge tube. This tube was centrifuged again and the white blood cell layer was removed and diluted with PBS.

White blood cell samples spiked with melanoma suspended in PBS were prepared by first obtaining whole blood donated from lab members. The blood was again poured into a centrifuge tube that contained Histopaque 1077. Cultured melanoma cells from the HS 936 line were added into the same centrifuge tube. The centrifugation process and the separation procedure remained the same as the White Blood Cell preparation above. The melanoma cells and white blood cells settle to the same layer after centrifugation due to their similar densities.

This layer was isolated and diluted with PBS.

EXAMPLE 4

Flow Chamber Design

The photoacoustic multi-phase flow system utilized a PVDF piezoelectric transducer while the laser struck at 90° from the transducer element. The alternative is to introduce laser light along the axis of flow utilizing the optical waveguide nature of the system. A single cell is considered an optical point source and will therefore emit photoacoustic waves radially in all directions equally. The flow chamber was held together with an acrylic ring that had three holes drilled at 90° from each other. Masterflex tubing was fed through the holes and a wire with the same outer diameter as the tubing's inner diameter was suspended through the two opposing holes while a second wire was fed through the third hole to prevent acrylamide from entering the tubing hole.

Once the acrylic ring was prepared, Parafilm was stretched across the bottom of the ring and clear acrylamide was poured into the ring, gelling around the tubing and wire. The acrylamide was made from 10 mL of 20% acrylamide solution (Sigma Aldrish), 0.04 g of ammonium persulfate (Sigma Aldrich) and 20 μL of TEMED (Fisher Scientific). After adding the TEMED, the mixture was poured immediately to avoid premature gelling.

After gelling, the wires were removed and the tubing used to hold the optical fiber was pulled out approximately 4 mm. The flow chamber was then ready to be used in the system.

EXAMPLE 5

Blind Study

In order to prove that any clinician can successfully operate this system, a blind study was performed to determine if samples that do not contain melanoma can be easily distinguished from samples that do contain melanoma.

Twenty random Boolean values were obtained using a short program made in MATLAB: "0" represented PBS+2% w/v Tween 20 solution, and "1" represented 10 melanoma cells/μL suspended in PBS+2% w/v Tween 20.

Two scientists initially prepared the samples without revealing which samples contained melanoma and which samples did not. Then two different scientists ran the samples through the flow system and were asked to determine which samples had melanoma cells and which did not based on the photoacoustic waves that were seen on the oscilloscope.

Figure 6:
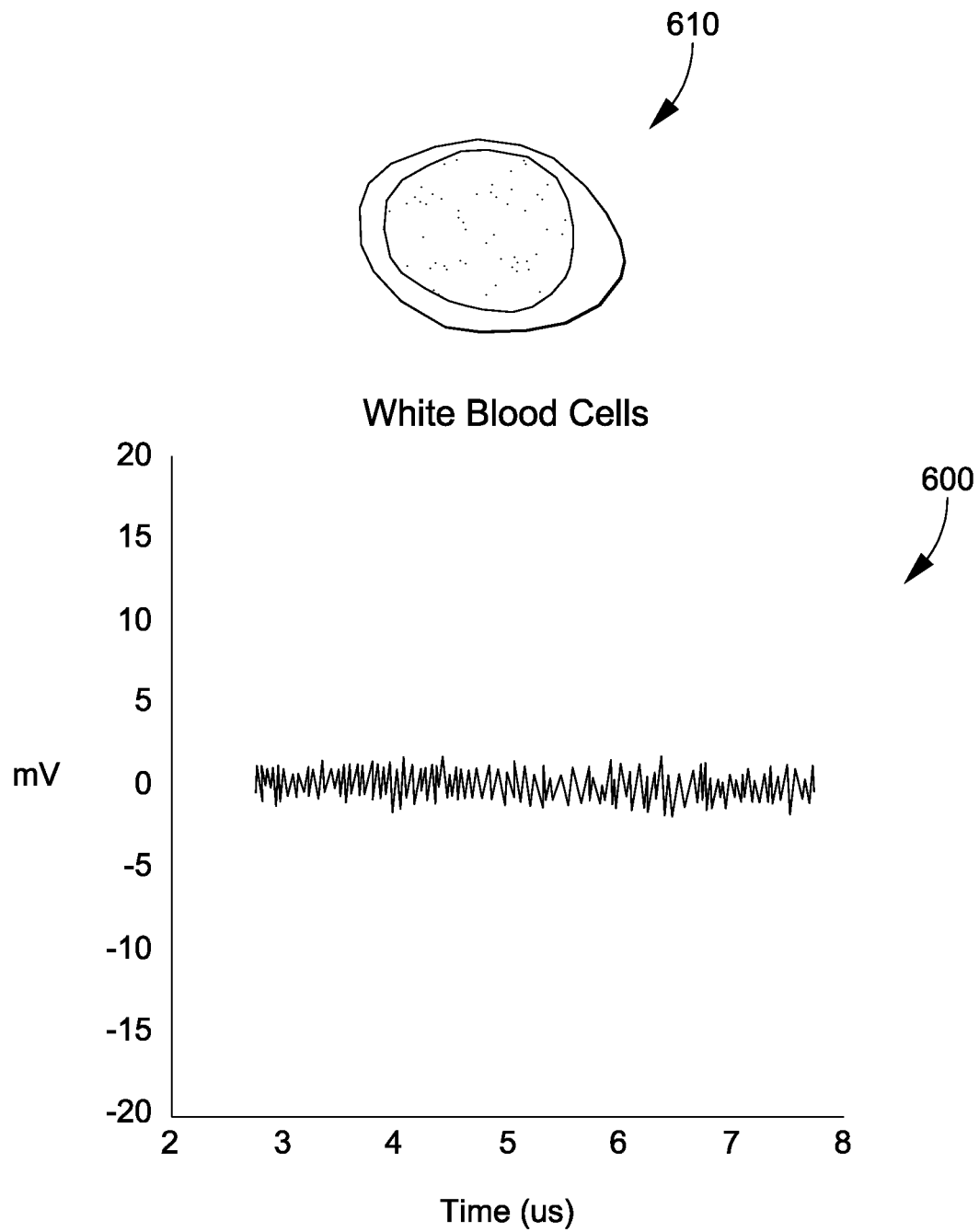
FIG. 6 is a graphical view of a photoacoustic amplitude of a sample of irradiated white blood cells, with an isolated droplet of the cell suspension showing a white blood cell, in accordance with embodiments of the invention.
Figure 7:
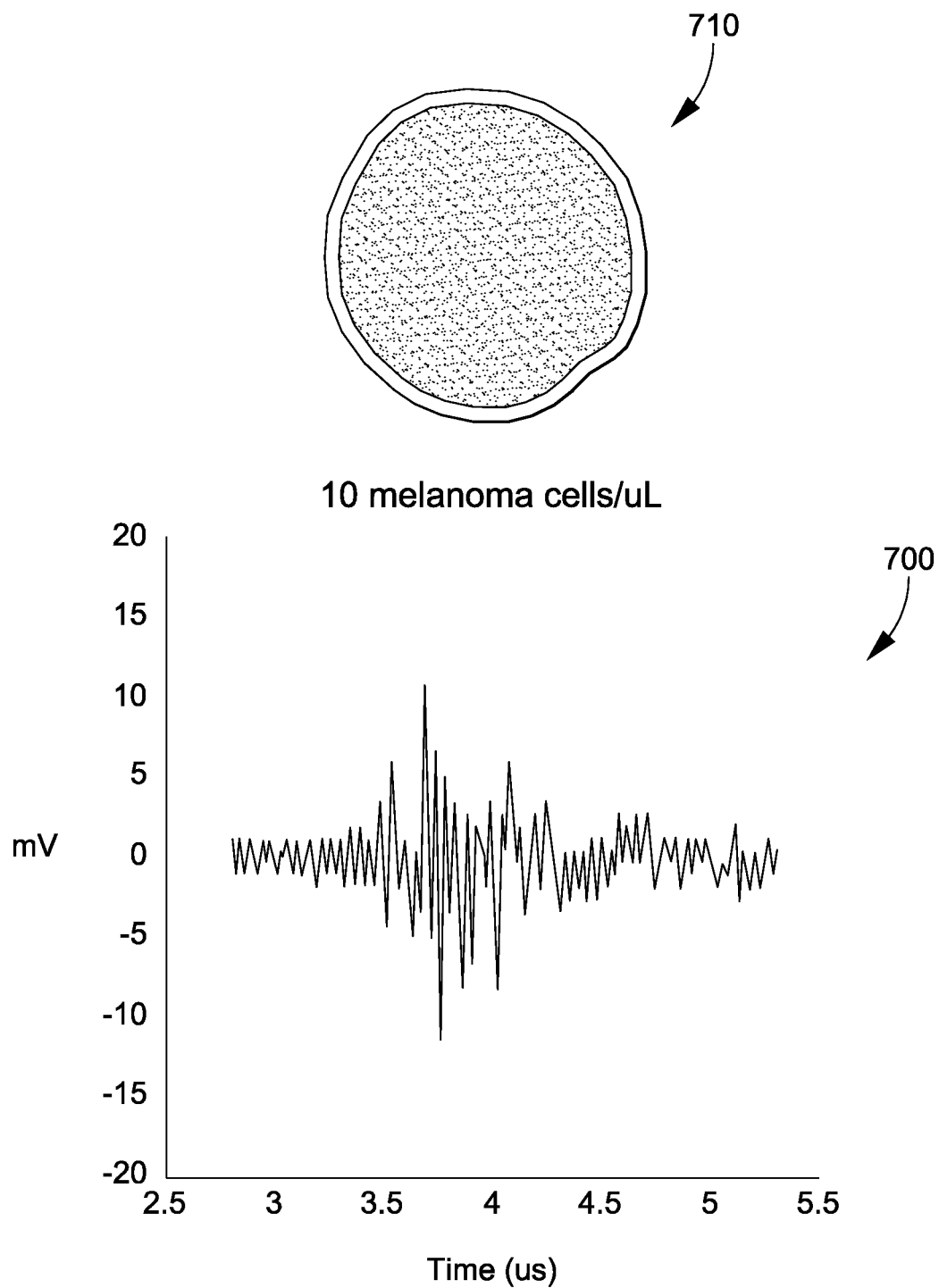
FIG. 7 is a graphical view of a photoacoustic amplitude of a sample of irradiated melanoma cells among white blood cells, with an isolated droplet of the cell suspension showing the presence of pigmented melanoma cells, in accordance with embodiments of the invention.

The scientists correctly identified all 20 samples, as seen in Table 1. Photoacoustic signals of a baseline and a detected cell sample are shown in FIGS. 6 and 7. In addition to larger amplitudes, melanoma cells produce transient signals while baseline peaks remain constant throughout flow.

TABLE 1

The 20 random Boolean values used for blind study.

| Sample # | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Content | 1 | 1 | 0 | 1 | 1 | 0 | 0 | 1 | 1 | 1 | 0 | 1 | 1 | 0 | 1 | 0 | 0 | 1 | 1 | 1 |
| Test Results | + | + | − | + | + | − | − | + | + | + | − | + | + | − | + | − | − | + | + | + |

EXAMPLE 6

Photoacoustic Detection and Capture of Melanoma Amongst WBCs

The flow system was prepared using three separate inlets: one syringe pump contained air, one syringe pump contained WBCs in PBS+Tween 20, and one syringe contained cultured melanoma cells in PBS. The WBC+PBS and air formed slugs throughout the system and were used to show that no photoacoustic signals were produced from either air or WBC bubbles. The syringe pump containing white blood cells was stopped and the syringe that contained melanoma was used to manually introduce a melanoma bubble into the flow system in hopes to create photoacoustic waves and then be isolated from the system.

Results
Two-phase flow: Water and oil.

It was observed that two phase flow using oil and air produced uniform, consistent bubbles without any backlogging of the flow system. Water and air.

It was observed that two phase flow using water and air produced inconsistent flow and pressure buildup occasionally purged the flow system.

After 2% Tween 20 was added to the water, consistent and uniform bubbles were produced without undergoing any backlogging.

EXAMPLE 7

Photoacoustic Melanoma Signals by Concentration

The system produced a photoacoustic signal from the melanoma bubbles and remained baseline for the WBC and air bubbles as seen in FIGS. 5A-5F. The detected melanoma bubble was then isolated as it dripped out of the system and the bubble was imaged along with a control WBC bubble.

Figure 5A:
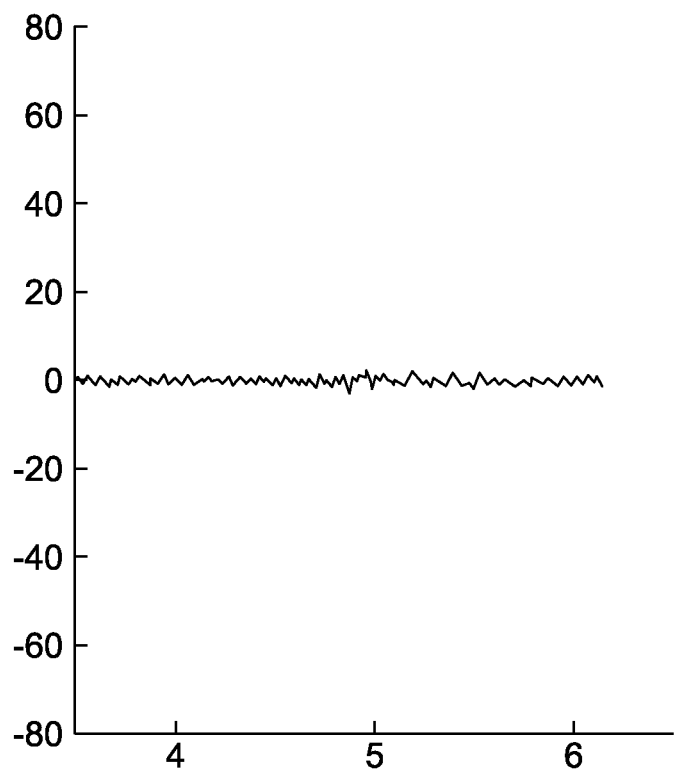
FIG. 5A-5F are graphical views of photoacoustic amplitudes of a number of samples in accordance with embodiments of the invention.
Figure 5B:
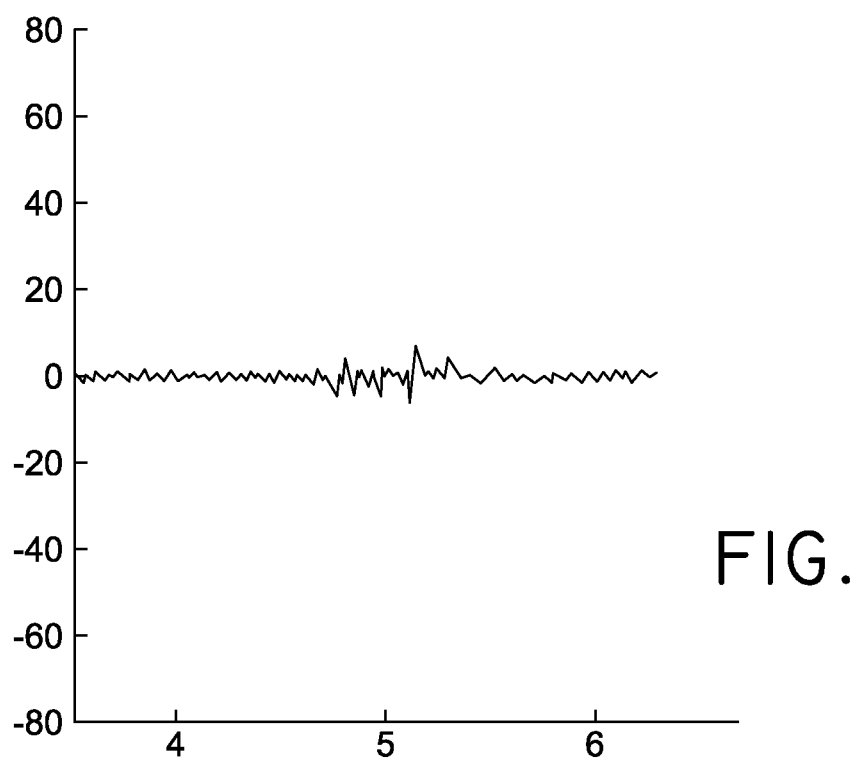
Figure 5C:
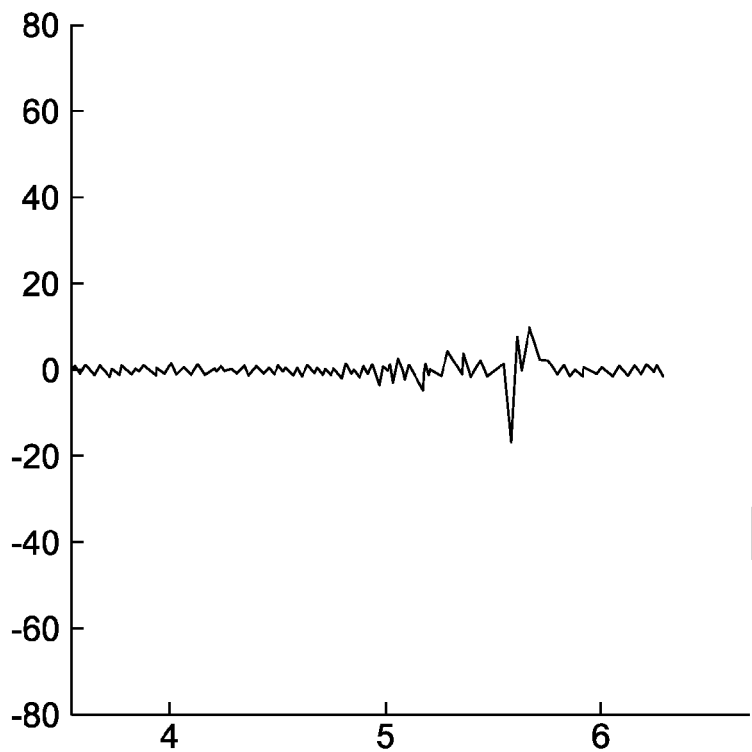
Figure 5D:
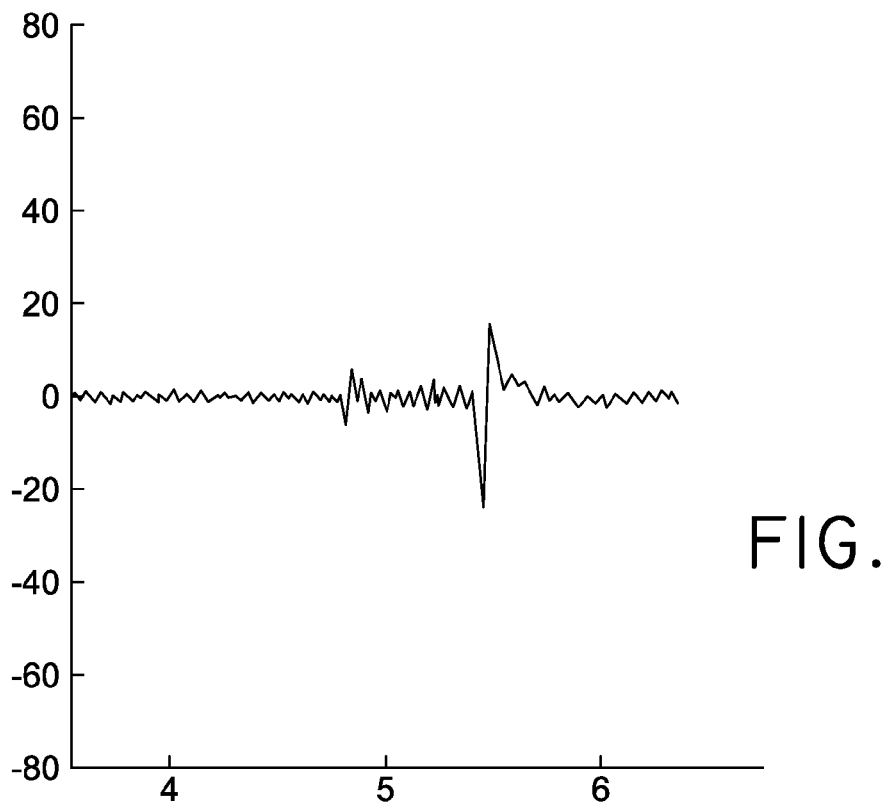
Figure 5E:
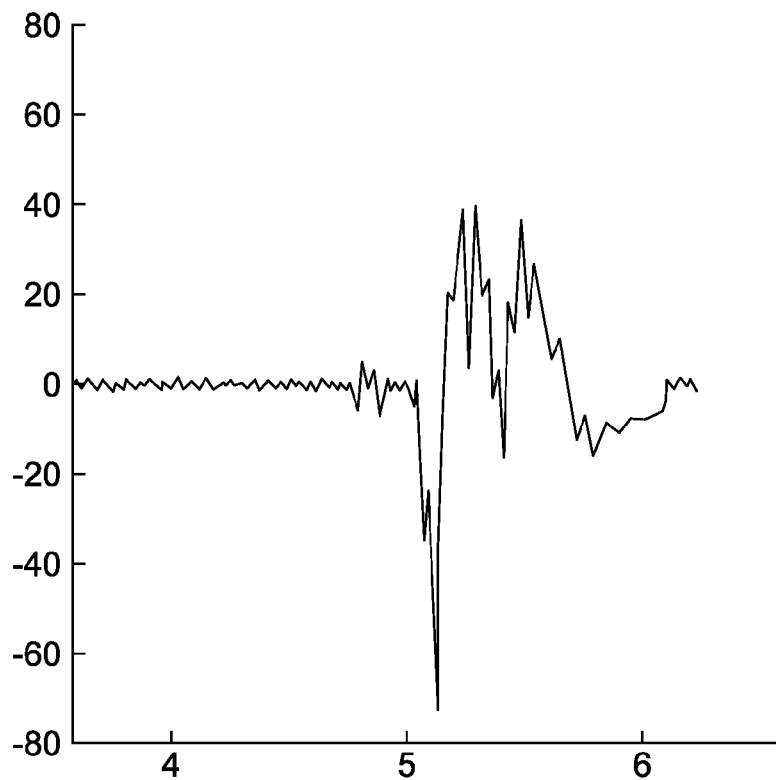

FIGS. 5A-5E are graphical representations of photoacoustic signals from different melanoma cell concentrations of discrete compartment detected utilizing the multi-phase flow system described above. FIGS. 5A-5E are plotted as photacoustic amplitude (mV) v. time (μs). FIG. 5A is a graphical representation of photoacoustic signals from a melanoma cell-free sample. FIG. 5B is a graphical representation of a photoacoustic signal from a sample containing 10 cells/μL of melanoma. FIG. 5C is a graphical representation of a photoacoustic signal from a sample containing 25 cells/μL of melanoma. FIG. 5D is a graphical representation of a photoacoustic signal from a sample containing 100 cells/μL of melanoma. FIG. 5E is a graphical representation of a photoacoustic signal from a sample containing 800 cells/μL of melanoma.

Figure 5F:
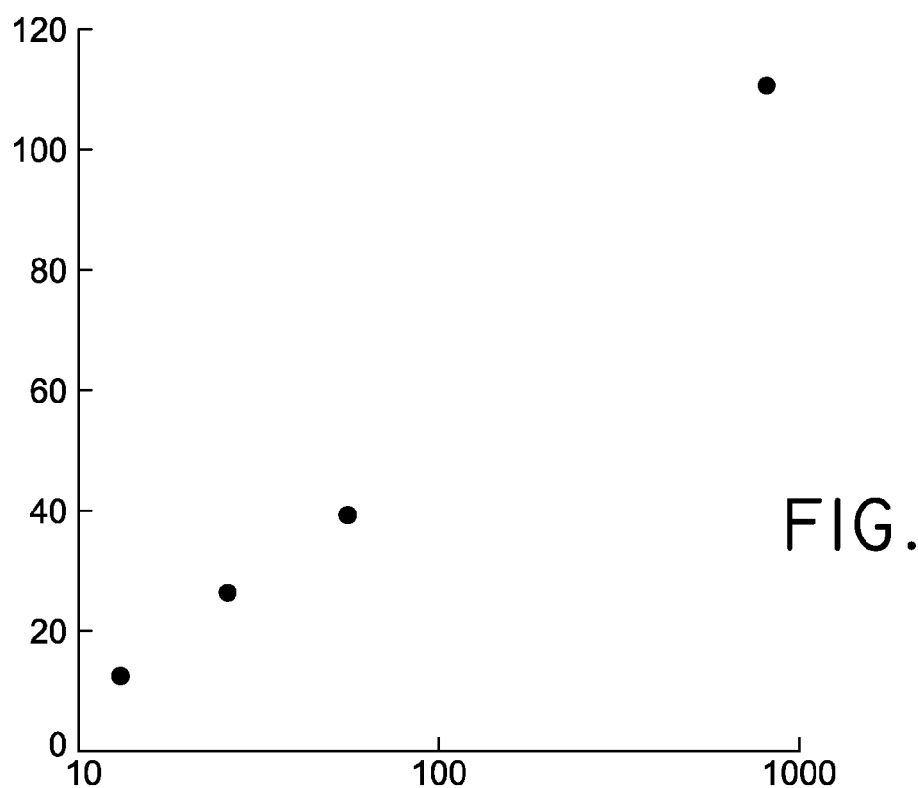

FIG. 5F is a graphical representation of plot of voltage response vs. cell concentration. The amplitude of photoacoustic signals followed linearly with concentration until concentrations of 10 cells/μL as shown in FIG. 5F.

Although successful bubble formation was achieved using both oil/water and air/water+surfactant, due to the ease of which melanoma cells can be extracted from the flow system, water and air with the addition of a surfactant will be the choice fluids for further studies. The addition of Tween 20 was effective due to its ability to decrease interfacial tension between the two phases allowing water to slide past the air when pressure built up.

The concentration study showed a linear correlation between voltage amplitude and concentration until very low concentrations were investigated. This was expected because the cells do not disseminate homogenously, which is made apparent at low concentrations. Also, as expected the PBS+Tween 20 control did not produce any photoacoustic signals.

The blind study confirmed that this method can be used in a clinical setting to detect melanoma. The melanoma cell capture further proved that the system can effectively isolate detected melanoma cells from the system. In addition, this is a significant step towards both an efficient disease monitoring technique and will enable scientists to study these metastatic cells in hopes of discovering the mechanisms by which they metastasize, survive in the blood and lymphatic systems, and settle in other tissues, so that better therapies for cancer patients and other types of disease can be developed.

EXAMPLE 8

Capture and Isolation of Melanoma

The system produced no signals for the PBS baseline, and produced photoacoustic signals from each different concentration of melanoma slugs. FIGS. 6 and 7 show the photoacoustic response of 1 melanoma cell/μL compared to the PBS baseline. Slugs that produced photoacoustic signals were isolated and then stained using the Fontana Masson stain, but the best results were from the 100 cells/μL samples, most likely due to the harsh staining procedure that require the slides to be washed numerous times, the nucleus stained red and melanin stained black. As shown in FIG. 6, a graphical view 600 of a photoacoustic amplitude of a sample of irradiated white blood cells yields no photoacoustic effect, with an isolated droplet of the cell suspension showing a white blood cell 610. In FIG. 7, a graphical view 700 of a photoacoustic amplitude of a sample of irradiated melanoma cells among white blood cells yields photoacoustic waves. An isolated droplet of the cell suspension showing photoacoustic waves indicates the presence of pigmented melanoma cells 710.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

We claim:

1. A multiple flow system for detecting substances in a fluid, the system comprising:
   a first fluid tube containing a first fluid, wherein the first fluid comprises a first type of analyte and a second type of analyte;
   a second fluid tube containing a second fluid, wherein the first fluid is different from the second fluid, wherein the first and second fluids are immiscible;
   a common fluid tube;
   a connector coupled to the first fluid tube, the second fluid tube, and the common fluid tube, wherein fluid flows from the first fluid tube and the second fluid tube into the common fluid tube via the connector such that alternating discrete compartments of the first fluid and the second fluid flow through the common fluid tube; and
   a substance detector coupled to the common fluid tube, the substance detector configured to receive each alternating discrete compartment and analyze each alternating discrete compartment, wherein the substance detector comprises a flow chamber having an internal wall, wherein the internal wall is made of acrylamide gel that provides an acoustic path from an excited cell to an acoustic sensor, wherein the alternating discrete compartments flow through the flow chamber and are analyzed by the substance detector such that the substance detector is configured to identify a first signal corresponding to detection of the first type of analyte and a second signal corresponding to the second type of analyte, wherein the substance detector comprises a photoacoustic laser, wherein the photoacoustic laser is directed transversely to the flow or along the axis of the flow using an optical waveguide to irradiate the entire discrete compartments, wherein the multiple flow system is for photoacoustic detection of circulating tumor cells.

2. The system of claim 1, wherein the substance detector further comprises:
   a pulsator.

3. The system of claim 2, wherein the laser is a photoacoustic laser, wherein the substance detector is configured to detect substances in the discrete compartments of the first and second fluids flowing through the flow chamber using imaging generated with the photoacoustic laser.

4. The system of claim 1, further comprising a third fluid tube containing a third fluid, wherein the third fluid tube is coupled to the connector, wherein fluid flowing from the second and third fluid tubes combines to form a mixture of fluids, wherein alternating discreet compartments of the mixture of fluids flows through the common tube separate from alternating discrete compartments of the first fluid flowing through the common fluid tube.

5. A multiple flow system for detecting substances in a fluid, the system comprising:
   at least one device for movement of fluid;
   a first fluid tube containing a first fluid;
   a second fluid tube containing a second fluid, wherein the first fluid and the second fluid are immiscible;
   a common fluid tube,
   a connector coupled to the first fluid tube, the second fluid tube, and the common fluid tube, wherein the common fluid tube is configured to receive the first fluid flowing from the first fluid tube and the second fluid flowing from the second fluid tube via the connector, wherein receiving the first fluid flowing from the first fluid tube and the second fluid flowing from the second fluid tube via the connector comprises generating alternating discrete compartments of the first fluid and the second fluid, wherein the alternating discrete compartments of the first and second fluids flow through the common fluid tube; and
   a substance detector coupled to the common fluid tube, wherein the alternating discrete compartments are analyzed by the substance detector, wherein the substance detector comprises a flow chamber having an internal wall, wherein the internal wall is made of acrylamide gel that provides an acoustic path from an excited cell to an acoustic sensor, wherein the substance detector comprises a photoacoustic laser, wherein the photoacoustic laser is directed transversely to the flow or along the axis of the flow using an optical waveguide to irradiate the entire discrete compartments, wherein the multiple flow system is for photoacoustic detection of circulating tumor cells.

6. The system of claim 5, wherein the second fluid has an index of refraction that is increased to an index of refraction higher than an index of refraction of the acrylamide gel.

7. The system of claim 5, wherein the substance detector further comprises:
   a pulsator.

8. The system of claim 7, wherein the laser is a photoacoustic laser, wherein the substance detector is configured to detect substances in fluid flowing through the flow chamber using imaging generated with the photoacoustic laser.

9. The system of claim 5, further comprising:
   a third fluid tube containing a third fluid, wherein the third fluid tube is coupled to the connector.

10. The system of claim 9, wherein the third fluid mixes with the second fluid to form a mixture of fluids, wherein the mixture of fluids does not mix with the first fluid, wherein alternating discrete compartments of the mixture of fluids and alternating discrete compartments of the first fluid flow along a single flow path in the common fluid tube, wherein the alternating discrete compartments of the mixture of fluids and the first fluid are analyzed by the substance detector.

11. A method for photoacoustic detection of circulating tumor cells in a fluid, the method comprising:
   receiving and passing a first fluid from a first fluid tube via a connector;
   receiving and passing a second fluid from a second fluid tube via the connector, wherein the first and second fluids are immiscible, wherein receiving and passing the first and second fluids via the connector comprises receiving and passing alternating discrete compartments of the first fluid and the second fluid to a substance detector;
   based on receiving the alternating discrete compartments, detecting at least one substance in one or more of the received alternating discrete compartments using the substance detector, wherein the substance detector comprises a photoacoustic laser, wherein the photoacoustic laser is directed transversely to the flow or along the axis of the flow using an optical waveguide to irradiate the entire discrete compartments;

extracting at least one discrete compartment; and diluting and re-passing the at least one extracted discrete compartment until each separate extraction volume of the second fluid contains a single tumor cell.

12. The method of claim 11, wherein receiving alternating discrete compartments of the first fluid and the second fluid comprises receiving the alternating discrete compartments of the first fluid and the second fluid via a common fluid tube coupled to the connector.

13. The method of claim 11, wherein the substance detector comprises a flow chamber having an internal wall, wherein the alternating discrete compartments of the first fluid and the second fluid flow through the flow chamber.

14. The method of claim 13, wherein the flow chamber is made from a material having an acoustic impedance close to an acoustic impedance of water.

15. The method of claim 14, further comprising increasing an index of refraction of the second fluid to an index of refraction that is higher than an index of refraction of the material.

16. The method of claim 13, wherein the substance detector further comprises:
   an excitation device for analyzing the received alternating discrete compartments;
   and
   a pulsator.

17. The method of claim 16, wherein the excitation device is a photoacoustic laser source.

* * * * *